United States Patent [19]

Honda et al.

[11] Patent Number: 4,980,162

[45] Date of Patent: Dec. 25, 1990

[54] LIVE VACCINE FOR CONTAGIOUS DISEASES OF CHICKENS

[75] Inventors: Takashi Honda; Akira Taneno; Takuma Hanaki; Masanobu Eto, all of Kumamoto, Japan

[73] Assignee: Juridical Foundation the Chemosero-Therapeutic Research Institute, Kumamoto, Japan

[21] Appl. No.: 74,148

[22] Filed: Jul. 16, 1987

[30] Foreign Application Priority Data

Jul. 17, 1986 [JP] Japan ................... 61-170188

[51] Int. Cl.$^5$ .................. A61K 39/12; C12N 7/00
[52] U.S. Cl. .................... 424/89; 435/235; 435/236; 435/237; 435/238; 435/239
[58] Field of Search .............. 424/89; 435/235-239

[56] References Cited

U.S. PATENT DOCUMENTS

| | | | |
|---|---|---|---|
| 3,642,574 | 2/1972 | Okazaki et al. | 424/89 |
| 3,981,771 | 9/1976 | Sevoian et al. | 424/89 |

FOREIGN PATENT DOCUMENTS 57-167925 10/1982 Japan .

OTHER PUBLICATIONS

Japanese Pat. No. 57,167,925 (82,167,925), "Preparation of mixed vaccines from the control of diseases in chickens", Chemical Abstracts, vol. 98, p. 341, Ref. #22260k, 1983.

Rossi et al, "Studies of Laryngotra cheitis virus in avian tissue cultures III. Enhancement of infectivity by DEAE-D," Chemical Abstracts, vol. 73, p. 91, ref. #5325x, 1970.

Shornikov et al, "lysozyrme activity of blood serum of chicks vaccinated agaisnt ILT by inhalation method," Chemical Abstracts, vol. 84, p. 246, ref. #71789j, 1976.

Hirai et al, "Comparative Studies on Marek's Disease Virus and Herpesvirus of Turkey DNAS," J. gen. Virol. vol. 45, pp. 119–131, 1979.

Van Zaane et al, "Molecular-Biological characterization of Marek's disease virus," Virology, vol. 121, pp. 133–146, 1982.

Gibbs et al, "Extensive homology exists between marek's disease herpesvirus and its vaccine virus, herpesvirus of turkeys," Proe. Natl. Acad. Sci., U.S.A., vol. 81, pp. 3365–3369, 1984.

Davis et al, "Ultrastructural Comparison of Morphogenesis and fate of Marek's disease and Inafectious Laryngotrocheitas Viruses in chicken Kidney Cells" Amer. J. Vet. Res. 34 (7): 873–880, Jul. 1973.

"Immunication Against Marek's Disease Using A Live Attenuated Virus", Churchill et al., Nature, vol. 221, pp. 744–747 (Feb. 22, 1969).

*Primary Examiner*—Margaret Moskowitz
*Assistant Examiner*—Abdel A. Mohamed
*Attorney, Agent, or Firm*—Fleit, Jacobson, Cohn, Price, Holman & Stern

[57] ABSTRACT

A live vaccine for infectious laryngotracheitis, which comprises culture cells infected with attenuated infectious laryngotracheitis virus. Also, a live combined vaccine for infectious laryngotracheitis and Marek's disease, which comprises culture cells infected with attenuated viruses off these two diseases. These vaccines can be used on day-old (newborn) chicken, by subcutaneous or intramuscular injection, to give them immunity from infection by the virus or viruses.

4 Claims, No Drawings

LIVE VACCINE FOR CONTAGIOUS DISEASES OF CHICKENS

TECHNICAL FIELD

The present invention relates to disease prevention in poultry, particularly in chickens. More particularly, it relates to a live infectious laryngotracheitis vaccine using culture cells and to a live combined vaccine for infectious laryngotracheitis and Marek's disease.

PRIOR ART

Infectious laryngotracheitis and Marek's disease are contagious diseases of chickens caused by viruses. These diseases are becoming a major problem in many parts of the world, including Japan, North America, Europe and Australia, where large-scale chicken breeding is highly developed. In such areas, these diseases have become a major factor in reducing the productivity of the poultry industry.

Infectious laryngotracheitis is a disease of the respiratory organs. Chickens infected with the infectious laryngotracheitis virus begin to show symptoms two or three days after infection and the symptoms persist for about two weeks. The mortality rate ranges between 10% and 70%, depending on the condition of the virus activity and breeding circumstances. It is generally about 20%. Further-more, sensibility of chickens to the virus is not influenced by lineage, sex or age. However, the symptoms tend to be more pronounced and the mortality rate higher among younger chickens.

Symptoms of chickens contracting the disease are sneezing and coughing caused by inflammation of the trachea. In serious cases, there is panting and death from suffocation caused by clogging of the trachea with an exudate. As a result, this disease causes high mortality, low breeding efficiency, decreased weight gain rates and decreased egg laying. In countries where chickens are bred on a large scale, infectious laryngotracheitis has been identified as a cause of reduced productivity of the chicken industry because of the great loss for chicken breeders in the case of the occurrence of infections laryngotracheitis in chickens on the farm.

On the other hand, Marek's disease is a malignant lymphoproliferative disease of chickens and its symptoms appear widely, in the nerves, genital organs, internal organs, eyes, skin and so on.

In addition, chickens have sensitivity to this virus with no influence of lineage or sex. However, it is reported that younger chickens have a higher sensitivity and suffer greater damage from the virus. The symptoms of Marek's disease include motor trouble caused by nerval paralysis in the case where the nerves have been affected, and functional trouble of the internal organs caused by tumor, and chronic consumptius undernourishment in the case the internal organs are attacked. The chickens usually die.

There are no effective therapeutic drugs for treatment of infectious laryngotracheitis or Marek's disease. Possible countermeasures include reduction of the number of chickens by removal of those which have been infected, and increased ventilation. However these measures are not substantially effective. The only realistic treatment for the diseases is use of an effective vaccine capable of protecting chickens from infection by the viruses.

Several vaccines for each disease have been developed and put to use. However, no combined vaccine for both diseases is available at present. Therefore, two vaccinations (one for each disease) are given.

The existing vaccine for infectious laryngotracheitis is still unsatisfactory in terms of safety, effectiveness and the method of injection.

The vaccine available at present for infectious laryngotracheitis is a live attenuated vaccine comprising a virus solution which is prepared in a culture medium by cultivation of culture cells infected with infectious laryngotracheitis virus. The chickens are vaccinated by dropping a lotion containing the vaccine into the eyes, which is one of the infection routes of the virus. The vaccine has problems as regards immunogenicity and immunization timing. Namely, the vaccine has nearly no effect for young chickens under 14 days old. Thus, there is no way to protect the chickens that have been infected with the virus before reaching 14 days. Additionally, chickens older than 14 days experience additional stress when caught for vaccination. Moreover, they can move about quite quickly at this age. So that much work is needed to catch them. The vaccination work thus becomes a major burden for breeders who raise a large number of chickens. Furthermore, there still remains the possibility that the vaccine applied to the eyes may have side effects, although there is less chance of this than in the past.

On the other hand, the existing vaccine for Marek's disease comprises infected culture cells containing cultured attenuated Marek's disease virus or herpes virus of turkey as its effective component and is usually used on newborn chickens just after hatching. Infected culture cells are used as the effective component of the vaccine because of the instability of the virus. When the virus appears outside the culture cell during cultivation, it rapidly changes and loses its antigenicity as a vaccine.

Thus, neither a satisfactory vaccine for infectious laryngotracheitis nor a satisfactory combined vaccine for infectious laryngotracheitis and Marek's disease has been developed heretofore.

OBJECTS OF THE INVENTION

It is an object of the invention to provide an improved infectious laryngotracheitis vaccine usable on day-old chickens. It is another object of the invention to provide an infectious laryngotracheitis vaccine which, like the existing Marek's disease vaccine, can be used by injection under the skin. It is a further object of the invention to provide a combined vaccine for infectious laryngotracheitis and Marek's disease.

THE INVENTION

These and other objects of the invention are achieved by providing a novel live infectious laryngotracheitis virus vaccine comprising as the effective component culture cells infected with the virus obtained by cultivation of attenuated infectious laryngotracheitis virus using culture cells.

While Marek's disease virus is exceptional in having the special characteristics describe above, most vaccines using ordinary virus comprise only the purified virus required as the effective component and are removed of other components such as culture cells, which are considered unnecessary. However, the inventors injected chickens with culture cells infected with infectious laryngotracheitis virus and unexpectedly found that the cells constituted a very effective vaccine which can be injected subcutaneously.

The present invention is based on this discovery. In further studies, the inventors confirmed that the present vaccine is extremely safe for use on chickens.

In other words, the inventors found an infectious laryngotracheitis vaccine for chickens which is effective and free from side effects and which need not be administered by the ordinary method of intraocular instillation to chickens over 14 days old, but can be administered by injecting it under the skin or into the muscles of newborn chickens, which is an easy method for chicken breeders.

The present invention provides an attenuated live vaccine for infectious laryngotracheitis, which gives lifelong immunity by a single injection under the skin or into the muscles of a day-old chicken. Furthermore, it provides a live attenuated combined vaccine for infectious laryngotracheitis and Marek's disease, which comprises culture cells infected with attenuated infectious laryngotracheitis virus and culture cells infected with attenuated Marek's disease virus or with herpes virus of turkey, and gives persisting immunity in the same manner as described before.

CONSTRUCTION AND EFFECT OF THE INVENTION

In the present invention, ordinary culture cells which are used for cultivation of virus can be used as the culture cell for cultivating the infectious laryngotracheitis virus or the virus causing Marek's disease. For instance, there can be used kidney culture cells, chick embryo culture cells derived from chicken, or embryo cells derived from duck.

As the viruses used for cultivation in the present invention, for the infectious laryngotracheitis vaccine there can be used attenuated infectious laryngotracheitis virus, for instance, CE strain of chicken infectious laryngotracheitis virus, and for the Marek's disease vaccine there can be used attenuated Marek's disease virus or herpes virus of turkey.

After the culture cells have been infected with an appropriate amount of attenuated virus, virus cultivation is carried out under the ordinary conditions, for instance by culturing for four to five days at 37° C. using a culturing bottle or culturing tank. At the maximum multiplication period of virus cultivation, infected culture cells are trypsinized and harvested by centrifugation. The culture cell solution is added with bovine serum albumin, for example, to obtain a vaccine suspension comprising floating culture cells. The vaccine suspension is transferred to and preserved in vials after being subjected to such indispensable tests for a vaccine as the sterility test.

The vaccine can be preserved either in frozen or freeze-dried condition. Frozen vaccine is obtained by freezing in liquid nitrogen after suspending the culture cells with a frozen cryoprotective agent such as dimethylsulfoxide or glycerin. Freeze-dried vaccine is obtained by drying and freezing after suspending the culture cells with an appropriate frozen cryoprotective agent.

The virus content of the infectious larynogotracheitis of the present invention is from about $10^3$ to $10^5$ $TCID_{50}$.

The vaccine solution of the combined vaccine for infectious laryngotracheitis and Marek's disease can be prepared by mixing sufficient amounts of the respective types of the culture cells infected with the virus. These culture cells may be obtained from cultivations of the respective attenuated viruses using culture cells. The vaccine solution can also be prepared by simultaneous cultivation of the two kinds of virus. In such a live combined vaccine, the effectiveness of immunization is often reduced by an interaction between two different viruses or vaccine components. However the present combined vaccine has been confirmed as being free from interaction of two virus, and quite useful.

One major advantage of the present invention is that it enables vaccination for infectious laryngotracheitis for newborn chickens by injection under the skin or into the muscles. Namely, the existing vaccine for infectious laryngotracheitis can be used only with chickens over 14 days. Actually it is more suitable for chickens over 21 days, because it is fully effective only with chickens of over this age. On the other hand, the present invention provides a new vaccine which can prevent infection by infectious laryngotracheitis virus when used with newborn chickens. This new vaccine exhibits high immunization effect and safety, and thus can be used to great advantage by chicken breeders.

Generally, insufficient effectiveness is a problem in the case of vaccination to newborn chickens because of antibodies transferred from the mother. However, the present vaccine exhibits adequate immuno-efficiency effect even in the presence of the maternal antibodies in chickens injected with the vaccine. It is presumed that the culture cells, which cover the infectious laryngotracheitis virus, prevent adverse effect from the maternal antibodies.

In addition to greatly increased effectiveness, the present vaccine reduces the chicken breeder's work because the present vaccine can be used not only for chickens older than 14 days but also for newborn chickens while they are still rather inactive. As the existing vaccines for Marek's disease are given to chickens at zero day old, giving the present vaccination for laryngotracheitis at this time causes little extra work for the chicken breeder. Furthermore, if the two immunizations are given by use of the present combined vaccine, there is an even greater saving of work for the breeder.

The present invention will now be described in detail in the following Examples, which are not limitative.

EXAMPLE 1

Chick embryo culture cells derived from specific-pathogen-free (SPF) chickens nine to eleven days old, were harvested and trypsinized in a 0.25% trypsin solution to give a suspending culture cell solution of $2 \times 10^6$ cells/ml. The infectious laryngotracheitis virus CE strain was added to the suspending culture cell solution at the ratio of $10^3$ $TDIC_{50}$ virus cells per 100 ml of the culture cell solution to produce culture cells infected with the virus. The infected culture cell solution was divided into 100–150ml lots and placed in culture bottles and cultured for four to five days at 37° C. At that time, more than 80% of the culture cells reached a state of cytopathogenic effect(CPE); the culture cells were then trypsinized and harvested by centrifugation. (1500 r.p.m., 5 min.) The harvested culture cells were pooled and suspended in an MEM medium containing fetal bovine serum to produce a vaccine solution with a concentration of $10^7$ cells/ml. The obtained vaccine suspension was confirmed safe by sterility tests and the like. The vaccine solution was added to dimethylsulfoxide in a final concentration of 10v/v%, potassium benzylpenicillin in a final concentration of 100 unit/ml and streptomycin sulfate in a final concentration of 100μg/ml, then poured into ampoules. The vaccines in the ampoules were preserved in frozen condition at −100° C. in liquid nitrogen. 990ml of sterile water was added to 4.0g of casein hydrate, 7.965g of sodium chloride, 0.18g of disodium hydrogen phosphate, 1.53g of sodium dihydrogen phosphate and 0.025g of phenol red, then sterilized to give a diluent (diluting solution) for vaccine. The vaccine in each ampoule was diluted with this diluent before injection into chickens.

The vaccine was applied to healthy zero-day old chickens and 21-day old chickens to check the side effects of the vaccine. The vaccine applications were done by subcutaneous injection in the neck and injection into the muscles. The results are shown in Table 1 and Table 2.

under the skin of chickens. These chickens were subjected to intratrachea challenge with virulent infectious laryngotracheitis virus NS-175 strain, two to ten weeks after the vaccine application. As a futher control, the same virus challenge was given to a control group of chickens to which the vaccine had not been applied. All groups of chickens were observed for clinical symptoms for ten weeks. The results are shown in Table 3.

TABLE 3

| Group | Vaccine injection | | | Incidence of sympton (%)[2] | | | | |
|---|---|---|---|---|---|---|---|---|
| | Vaccine | Route | amount[1] | 2 w. | 4 w. | 6 w. | 8 w. | 10 w. |
| (1) | Present Vaccine | Subcutaneous | $10^{4.0}$ | 5 | 10 | 15 | 30[5] | 25[5] |
| (2) | Present Vaccine | Intramuscular | $10^{4.0}$ | 10 | 10 | 30 | 25[5] | 30[5] |
| (3) | Existing Vaccine | Subcutaneous | $10^{4.5}$ | 30 | 50 | 70 | 90[30] | 90[40] |
| (4) | Existing | Intraocular | $10^{4.5}$ | 10 | 65 | 70 | 75[30] | 85[30] |
| (5) | Control (non-application) | | — | 100 | 100 | 100 | 100[100] | 100[90] |

[1]Amount TCID$_{50}$
[2]Incidence of symptom after virus challenge
Numbers inside brackets show incidence of death or severe symptoms $$\text{Incidence} = \frac{\text{number of chickens showing symptoms}}{\text{number of test chickens}} \times 100(\%)$$

As is clear from the above results, the chickens to which the present vaccine was applied maintained enough immunity to be protected from the virus infection. On the contrary, every chicken to which the vaccine was not applied showed the characteristic symptoms of infectious laryngotracheitis. A large number of the chickens which had had the conventional vaccine

TABLE 1

| | Chickens | | Vaccine injection | | Clinical observations | | |
|---|---|---|---|---|---|---|---|
| | | | | | | Average weight | |
| Group | Age | Number | Route | Amount[1] | Appearance | 3 w.[2] | 10 w. (g) |
| (1) | 0 | 10 | Subcutaneous | $0.2(10^{4.5})$ | Normal | 163 | 771 |
| (2) | 0 | 10 | Intramuscular | $0.2(10^{4.5})$ | Normal | 163 | 796 |
| (3) | 0 | 10 | Control (non-application) | | Normal | 163 | 780 |

[1]Amount ml (TCID$_{50}$)
[2]weeks after the injection

TABLE 2

| | Chickens | | Vaccine injection | | Clinical observations | | |
|---|---|---|---|---|---|---|---|
| | | | | | | Average weight | |
| Group | Age | Number | Route | Amount[1] | Appearance | 3 w.[2] | 10 w. (g) |
| (1) | 21 | 10 | Subcutaneous | $0.2(10^{4.5})$ | Normal | 390 | 784 |
| (2) | 21 | 10 | Intramuscular | $0.2(10^{4.5})$ | Normal | 372 | 765 |
| (3) | 21 | 10 | Control (non-application) | | Normal | 374 | 781 |

[1]Amount ml (TCID$_{50}$)
[2]weeks after the injection

As is clear from the above results, no side effect of the vaccine was detected either in the zero-day old chickens or in the 21-day old chickens. These results positively demonstrate the safety of the vaccine.

Next, a virus challenge test was carried out on the chickens which had received the vaccine at zero-day old to confirm the effectiveness of the vaccine. The present vaccine was applied subcutaneously or intramuscalarly. As a control, a conventional vaccine for infectious laryngotracheitis was applied to the eyes or applied into their eyes or under the skin also showed the same symptoms. It is also clear from the above results that the chickens to which the present vaccine was applied showed quite low development of the symptoms when compared with the chickens to which the existing vaccine was applied. Furthermore, when symptoms did occur in the chickens which had been applied with the present vaccine, they were rather light. Very few chickens suffered symptoms. From these results, the present vaccine was confirmed to be very effective in preventing infection by infectious laryngotracheitis virus.

EXAMPLE 2

In the same manner as described in Example 1, infectious laryngotracheitis virus CE strain was added to chick embryo culture cells, which were then cultured to prepare culture cells infected with infectious laryngotracheitis virus. Then, other chick embryo culture cells were infected with the herpes virus of turkeys YT-7 strain and cultivated to prepare culture cells infected with the virus. These two kinds of culture cells were then mixed and suspended in an Eagle MEM medium containing fetal bovine serum. To the suspended culture cells was then added dimethylsulfoxide etc. to provide the combined vaccine in the same manner described in Example 1. The combined vaccine was placed in ampoules and preserved in liquid nitrogen.

The so-obtained combined vaccine was applied to zero-day old chickens and also to 21-day old chickens to check the safety of the vaccine. The vaccine applications were done by subcutaneous injection in the neck and intramuscular injection. The results are shown in Table 4 and Table 5.

As is clear from the above results, there were detected no side effects of the vaccine either in the zero-day old chickens or the 21-day old chickens. The results positively demonstrate the safety of the vaccine.

Next, the combined vaccine was applied to zero-day old chickens by subcutaneous injection in the neck or injection into the muscles. To confirm the effectiveness of the vaccine, these chickens were subjected to an intratrachea challenge with virulent infectious laryngotracheitis virus NS-175 strain, two to ten weeks after the vaccine application. As a control, chickens which had received a conventional vaccine for infectious laryngotracheitis and chickens which had received no vaccine at all were also given the same challenge. All groups of chickens were observed for clinical symptoms for ten weeks. The results are shown in Table 6. Furthermore, the chickens which had been applied with the present combined vaccine were also given intraperitoneal challenge with virulent Marek's disease virus Alabama strain, two weeks after the vaccine application. As a control, the same virus challenge was given to chickens which had received the conventional Marek's disease vaccine at zero-day old and to chickens which had received no vaccine. All groups of chickens were observed for clinical symptoms for ten weeks. The results are shown in Table 7.

TABLE 4

| | Chickens | | Vaccine injection | | Clinical observations | | |
|---|---|---|---|---|---|---|---|
| | | | | | | Average weight | |
| Group | Age | Number | Route | Amount (Contents)*1 | Appearance | 3 w.*2 | 10 w. (g) |
| (1) | 0 | 10 | Subcutaneous | 0.2(L:$10^{4.7}$, M:2000) | Normal | 170 | 768 |
| (2) | 0 | 10 | Intramuscular | 0.2(L:$10^{4.7}$, M:2000) | Normal | 172 | 777 |
| (3) | 0 | 10 | | Control (non-application) | Normal | 161 | 780 |

*1 Amount ml (L:TCID$_{50}$, M:PFU)
L: Amount of attenuated infectious laryngotracheitis virus CE strain
M: Amount of attenuated herpes virus YT-7 strain of turkey
*2 weeks after the injection

TABLE 5

| | Chickens | | Vaccine injection | | Clinical observations | | |
|---|---|---|---|---|---|---|---|
| | | | | | | Average weight | |
| Group | Age | Number | Route | Amount (Contents)*1 | Appearance | 3 w.*2 | 10 w. (g) |
| (1) | 21 | 10 | Subcutaneous | 0.2(L:$10^{4.7}$, M:2000) | Normal | 372 | 790 |
| (2) | 21 | 10 | Intramuscular | 0.2(L:$10^{4.7}$, M:2000) | Normal | 388 | 779 |
| (3) | 21 | 10 | | Control (non-application) | Normal | 374 | 781 |

*1 Amount ml (L:TCID$_{50}$, M:PFU)
L: Amount of attenuated infectious laryngotracheitis virus CE strain
M: Amount of attenuated herpes virus YT-7 strain of turkey
*2 weeks after the injection

TABLE 6

| | Vaccine injection | | | Incidence of symptom (%)*3 | | | | |
|---|---|---|---|---|---|---|---|---|
| Group | Route | L:(TCID$_{50}$) | M:(PFU)*1 | 2 w.*2 | 4 w. | 6 w. | 8 w. | 10 w. |
| (1) | Subcutaneous | $10^{4.7}$ | 2000 | 10 | 10 | 20 | 25 | 30 |
| (2) | Intramuscular | $10^{4.7}$ | 2000 | 5 | 15 | 25 | 20 | 35 |
| (3) | Intraocular | $10^{4.5}$ | 2000 | 10 | 65 | 70 | 75 | 85 |
| (4) | | Control | | 100 | 100 | 100 | 100 | 100 |

TABLE 6-continued

| Group | Vaccine injection Route | L:(TCID$_{50}$) | M:(PFU)[*1] | Incidence of symptom (%)[*3] 2 w.[*2] | 4 w. | 6 w. | 8 w. | 10 w. |
|---|---|---|---|---|---|---|---|---|
| | | (non-application) | | | | | | |

[*1]L: Amount of attenuated infectious laryngotracheitis vurus CE strain
M: Amount of attenuated herpes virus YT-7 strain of turkey
[*2]weeks after the injection
[*3]Incidence of symptom after virus challenge $$\text{Incidence} = \frac{\text{number of chickens showing symptoms}}{\text{number of test chickens}} \times 100(\%)$$

TABLE 7

| Group | Vaccine injection Route | L:(TCID$_{50}$) | M:(PFU)[*1] | Incidence of symptom[*2] |
|---|---|---|---|---|
| (1) | Subcutaneous | 10$^{4.0}$ | 2000 | 0% |
| (2) | Intramuscular | 10$^{4.0}$ | 2000 | 5% |
| (3) | Subcutaneous | — | 2000 | 10% |
| (4) | Control (non-application) | | | 100% |

[*1]L: Amount of attenuated infectious laryngotracheitis vurus CE strain
M: Amount of attenuated herpes virus YT-7 strain of turkey
[*2]Incidence of symptom after virus challenge $$\text{Incidence} = \frac{\text{number of chickens showing symptoms}}{\text{number of test chickens}} \times 100(\%)$$

As is clear from the above results, the chickens which were given the present combined vaccine maintained enough immunity to be protected from infection by infectious laryngotracheitis virus and / or Marek's disease virus. No loss of effect in immunization against the two virus infections was observed as a result of combining the two kinds of different culture cells which are the effective components of the combined vaccine.

What is claimed is:

1. A vaccine that is effective in preventing or treating ameliorating the symptons of infectious laryngotracheitis, comprising cultured cells that are infected with attenuated infectious laryngotracheitis virus, wherein said cultured cells are chicken embryo cells or chicken kidney cells and said vaccine is safe and effective for immunizing newborn or older chickens against infectionous laryngotracheitis.

2. A combined vaccine that is effective in preventing or treating the symptons of infectious laryngotracheitis and Marek's disease, comprising a mixture of cultured cells that are infected with attenuated infectious laryngotracheitis virus and cultured cells that are infected with attenuated Marek's disease virus or herpes virus of turkey, wherein said cultured cells are chicken embryo cells or chicken kidney cells are said vaccine is safe and effective for immunizing newborn or older chickens against infectious laryngotracheitis and against Marek's disease.

3. A method of vaccinating poultry for infectious laryngotracheitis comprising administering to said poultry an effective immunity producing amount of the vaccine of claim 1 by subcutaneous injection or intramuscular injection.

4. A method of vaccinating poultry for infectious laryngotracheitis and Marek's disease comprising administering to said poultry an effective immunity producing amount of the vaccine of claim 2 by subcutaneous injection or intramuscular injection.

* * * * *